(12) United States Patent
Nishio et al.

(10) Patent No.: US 7,244,025 B2
(45) Date of Patent: Jul. 17, 2007

(54) EYE'S OPTICAL CHARACTERISTICS MEASURING SYSTEM

(75) Inventors: Kouji Nishio, Itabashi-ku (JP);
Yasufumi Fukuma, Itabashi-ku (JP);
Katsuhiko Kobayashi, Itabashi-ku (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 35 days.

(21) Appl. No.: 11/402,736

(22) Filed: Apr. 12, 2006

(65) Prior Publication Data
US 2006/0256286 A1 Nov. 16, 2006

(30) Foreign Application Priority Data
May 16, 2005 (JP) ............................. 2005-142307

(51) Int. Cl.
*A61B 3/10* (2006.01)
(52) U.S. Cl. ...................................... 351/211; 351/205
(58) Field of Classification Search ................ 351/205, 351/241, 211, 210, 212, 246
See application file for complete search history.

(56) References Cited

U.S. PATENT DOCUMENTS 5,500,697 A * 3/1996 Fujieda ........................ 351/212
6,217,172 B1 * 4/2001 Shibutani et al. ........... 351/204
6,629,761 B1 * 10/2003 Hirohara et al. ............ 351/221
6,789,900 B2 * 9/2004 Van de Velde .............. 351/221
6,824,269 B2 * 11/2004 Takeuchi et al. ............ 351/214

FOREIGN PATENT DOCUMENTS

JP    1-129830    5/1989
JP    2002-209852    7/2002

* cited by examiner

*Primary Examiner*—Ricky Mack
*Assistant Examiner*—Tuyen Tra
(74) *Attorney, Agent, or Firm*—Nields & Lemack

(57) ABSTRACT

An eye's optical characteristics measuring system, comprising a first target projection optical system for projecting a target image on a fundus of an eye under test, a first photodetecting means for receiving the target image reflected from the fundus of the eye under test from the first target image projecting optical system, an ocular refractive power measuring unit for measuring ocular refractive power of the eye under test based on photodetection result from the first photodetecting means, a second target projecting means for projecting a spot-like target image to the fundus of the eye under test, a second photodetecting means for receiving the target image reflected from the fundus of the eye under test, and an eye's optical characteristics measuring unit for measuring ocular refractive power based on two or more images acquired at a predetermined refractive degree pitch before and after centering the refractive degree of the eye under test obtained by the second photodetecting means.

8 Claims, 5 Drawing Sheets

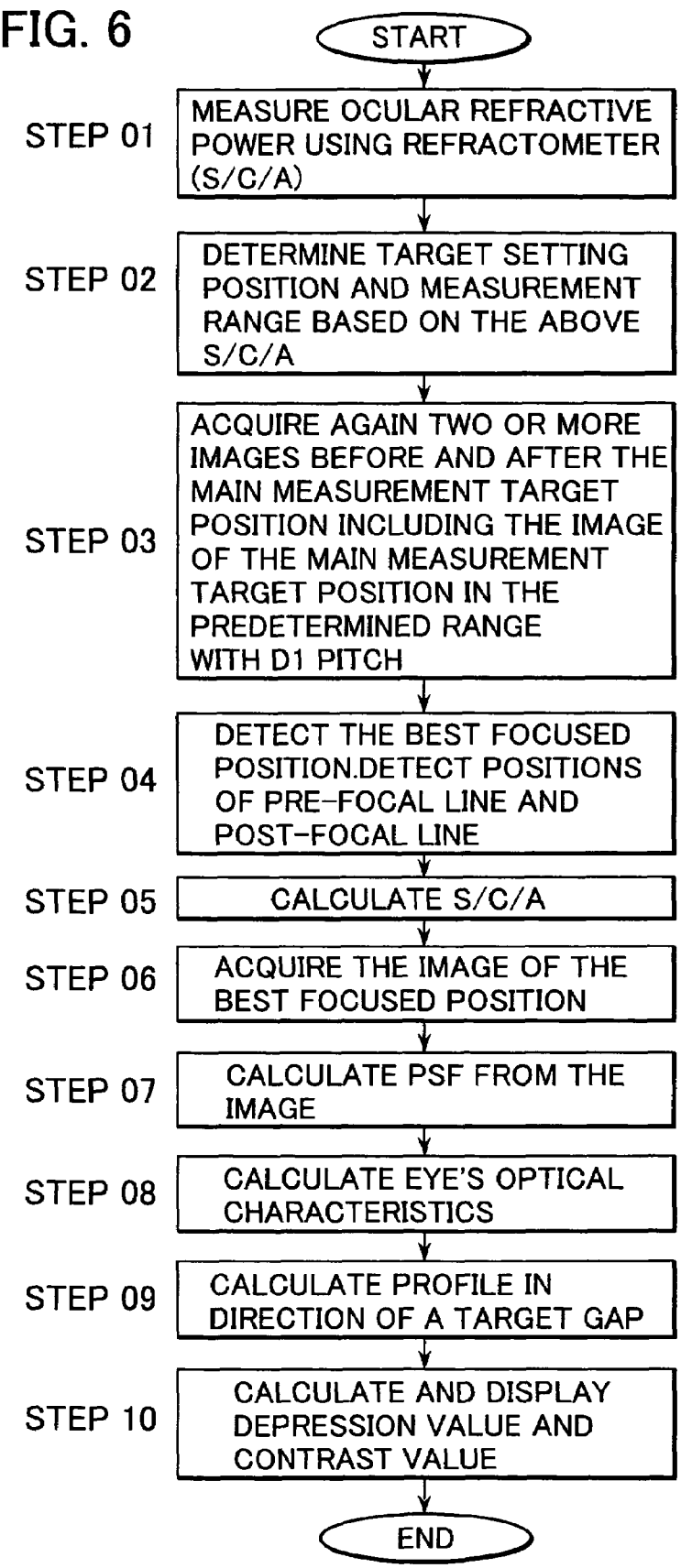

EYE'S OPTICAL CHARACTERISTICS MEASURING SYSTEM

BACKGROUND OF THE INVENTION

The present invention relates to an eye's optical characteristics measuring system for measuring ocular refractive power parameters and optical characteristics of an eye under test such as ocular refractive degree, astigmatic degree, astigmatic axis, etc.

In the past, as an ocular refractive power measuring system, there is an objective type ocular refractive power measuring system. By this system, a target image is projected to a fundus of an eye under test, and the target image reflected from the fundus of the eye under test is received by a photoelectric detector, and ocular refractive power parameters such as ocular refractive degree, astigmatic degree, astigmatic axis, etc. are measured from a received image.

In the objective type ocular refractive power measuring system as described above, when astigmatic parameters such as ocular refractive power (spherical refractive power), astigmatic degree (cylindrical refractive power), astigmatic axis, etc. are measured, a luminous flux in complete round ring form is projected to the fundus of the eye under test as the target image, and roundness (circularity) of the target image received by the photoelectric detector is detected. For instance, in case the eye under test has astigmatism, the received image is in elliptical shape. From the elliptical shape (flatness), astigmatic degree (C) can be obtained, and astigmatic axis angle A is measured from a tilt angle of the ellipse (tilt angle of longer axis of ellipse).

In the conventional type ocular refractive power measuring system, the luminous flux in ring form is projected for the measurement of ocular refractive power. As a result, a projected luminous flux and a reflected luminous flux are under influence of factors such as configuration of a cornea, an edema, turbidity of a crystalline lens, etc. Thus, there are such problems that the elliptical shape of the received image is collapsed and accurate measurement cannot be performed.

Further, in the conventional type ocular refractive power measuring system, it is not possible to objectively observe which kind of image is formed on the fundus of the eye under test.

As the ocular refractive power measuring system for measuring ocular refractive power by projecting the luminous flux in ring form, for instance, a system is shown in JP-A-1-129830.

SUMMARY OF THE INVENTION

It is an object of the present invention to provide an eye's optical characteristics measuring system, by which it is possible to accurately measure ocular refractive power even when there are configuration of a cornea, an edema, turbidity of a crystalline lens, etc. and to objectively observe an image formed on the fundus of the eye under test.

To attain the above object, the eye's optical characteristics measuring system according to the present invention comprises a first target projection optical system for projecting a target image on a fundus of an eye under test, a first photodetecting means for receiving the target image reflected from the fundus of the eye under test from the first target image projecting optical system, an ocular refractive power measuring unit for measuring ocular refractive power of the eye under test based on photodetection result from the first photodetecting means, a second target projecting means for projecting a spot-like target image to the fundus of the eye under test, a second photodetecting means for receiving the target image reflected from the fundus of the eye under test, and an eye's optical characteristics measuring unit for measuring ocular refractive power based on two or more images acquired at a predetermined refractive degree pitch before and after centering the refractive degree of the eye under test obtained by the second photodetecting means. Also, the present invention provides the eye's optical characteristics measuring system as described above, wherein spherical refractive power is measured based on an image having a least blurred circle among the two or more images. Further, the present invention provides the eye's optical characteristics measuring system as described above, wherein, among the two or more images, cylindrical refractive degree is measured from a difference between refractive degree corresponding to the image of a pre-focal line and refractive degree corresponding to the image of a post-focal line, and an astigmatic axis angle is measured based on configurations of the image of a pre-focal line and the image of the post-focal line. Also, the present invention provides the eye's optical characteristics measuring system as described above, wherein the eye's optical characteristics measuring unit comprises a calculating means for obtaining light intensity distribution based on the image acquired by the second photodetecting means and for calculating a simulation image of the target image projected on the fundus of the eye under test from the light intensity distribution thus obtained. Further, the present invention provides the eye's optical characteristics measuring system as described above, wherein the calculating means detects light intensity distribution characteristics in a predetermined meridional direction of the simulation image.

The present invention provides an eye's optical characteristics measuring system, which comprises a first target projection optical system for projecting a target image on a fundus of an eye under test, a first photodetecting means for receiving the target image reflected from the fundus of the eye under test from the first target image projecting optical system, an ocular refractive power measuring unit for measuring ocular refractive power of the eye under test based on photodetection result from the first photodetecting means, a second target projecting means for projecting a spot-like target image to the fundus of the eye under test, a second photodetecting means for receiving the target image reflected from the fundus of the eye under test, and an eye's optical characteristics measuring unit for measuring ocular refractive power based on two or more images acquired at a predetermined refractive degree pitch before and after centering the refractive degree of the eye under test as obtained by the second photodetecting means. As a result, ocular refractive power can be measured regardless of the conditions of the eye under test. This contributes to the improvement of accuracy in the measurement of refractive power. Because there is no individual difference in the results of measurement according to each examiner, the reliability of the measurement can be improved.

The present invention provides the eye's optical characteristics measuring system as described above, wherein the eye's optical characteristics measuring unit comprises a calculating means for obtaining light intensity distribution based on the image acquired by the second photodetecting means and for calculating a simulation image of the target image projected on the fundus of the eye under test from the light intensity distribution thus obtained. Therefore, it is possible to objectively observe the image, which would be formed on the eye under test.

Also, the present invention provides the eye's optical characteristics measuring system as described above, wherein the calculating means detects light intensity distribution characteristics in a predetermined meridional direction of the simulation image. As a result, it is possible to measure optical characteristics of the eye under test based on light intensity distribution characteristics.

BRIEF DESCRIPTION OF THE DRAWINGS

FIG. 6 is a flow chart to show processes of measurement of eye's optical characteristics in a second embodiment of the present invention.

DETAILED DESCRIPTION OF THE PREFERRED EMBODIMENTS

Figure 1:
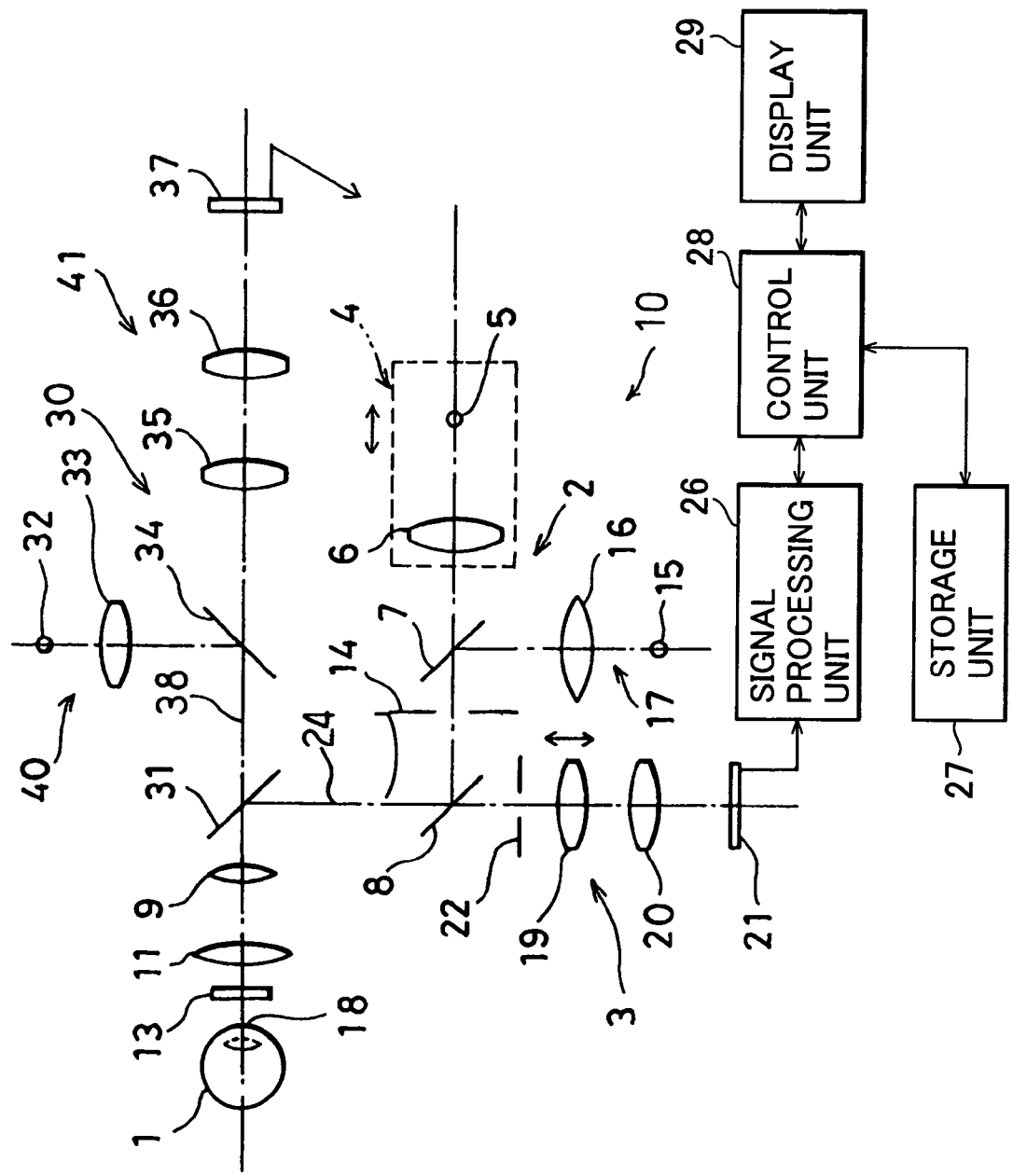
FIG. 1 is a schematical block diagram of an optical system in an embodiment of the present invention.

Description will be given below on the best mode for carrying out the invention referring to the drawings.

First, referring to FIG. 1, description will be given on an optical system of an eye's optical characteristics measuring system, in which the present invention is carried out.

In the figure, reference numeral 10 denotes an eye's optical characteristics measuring unit, and 30 denotes an ocular refractive power measuring unit. Reference numeral 1 denotes an eye under test. On an optical axis of the eye under test 1, a half-mirror 31 is arranged. By the half-mirror 31, the optical axis is divided to an optical axis 24 of the eye's optical characteristics measuring unit and an optical axis 38 of the ocular refractive power measuring unit.

First, description will be given on the eye's optical characteristics measuring unit 10.

The eye's optical characteristics measuring unit 10 comprises a projection optical system 2, a photodetection optical system 3, and a light source unit 4. The projection optical system 2 projects a spot-like target image to the eye under test 1, and the photodetection optical system 3 is designed to guide a target image reflected from a fundus of the eye under test 1 toward a photodetector (photoelectric detector) 21.

The eye's optical characteristics measuring unit 10 comprises a polarization beam splitter 8 arranged on the optical axis 24 of the eye's optical characteristics measuring unit, and the eye's optical characteristics measuring unit 10 is divided to the projection optical system 2 and the photodetection optical system 3 by the polarization beam splitter 8.

The projection optical system 2 comprises a light source 5, a relay lens 6 for converging a projected luminous flux emitted from the light source 5, a half-mirror 7 arranged on an optical axis of the relay lens 6, the polarization beam splitter 8 for directing the projected luminous flux passing though the half-mirror 7 toward the eye under test 1 and for reflecting and projecting a linearly polarized light component in a first direction of polarization (S-linearly polarized light), and a relay lens 9, an objective lens 11 and a ¼ wave plate 13 which are arranged on a projection optical axis of the polarization beam splitter 8 from the side of the polarization beam splitter 8.

A projection system aperture diaphragm 14 is provided at an adequate position on the projection optical system 2, e.g. between the half-mirror 7 and the polarization beam splitter 8. Further, a fixation target system 17 comprising a fixation target 15 and a relay lens 16 is arranged to face toward the half-mirror 7.

The light source 5 and the fixation target 15 are at positions conjugate to the fundus of the eye under test 1. As to be described later, images of the light source 5 and the fixation target 15 are formed on the fundus of the eye under test 1 via a pupil 18. The pupil 18 is at a position conjugate or approximately conjugate to the projection system aperture diaphragm 14. On the fixation target 15, a target for visual acuity test, e.g. a Landolt ring, is marked. The light source unit 4 comprises the light source 5 and the relay lens 6 are composed integrally. The light source unit 4 is interlocked with a focusing lens 19 as described later and is movable along the optical axis.

The photodetection optical system 3 shares the polarization beam splitter 8 and the relay lens 9, the objective lens 11 and the ¼ wave plate 13 which are arranged on the projection optical axis of the polarization beam splitter 8, with the projection optical system 2.

On an optical axis of the reflection light passing though the polarization beam splitter 8, a photodetection system aperture diaphragm 22, the movable focusing lens 19, and an image forming lens 20 are arranged along the optical axis of the reflection light, and the image forming lens 20 forms an image of the reflected luminous flux on the photoelectric detector 21. The photoelectric detector 21 and the fundus of the eye under test 1 are at positions conjugate or approximately conjugate to each other.

Figure 2:
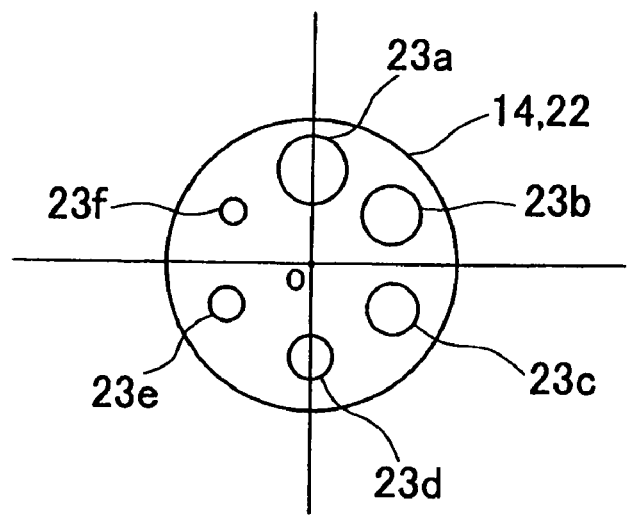
FIG. 2 is a drawing to show an example of an aperture diaphragm of a projecting system and an aperture diaphragm of a photodetection system to be used in the embodiment of the present invention.

FIG. 2 shows the projection system aperture diaphragm 14 and the photodetection system aperture diaphragm 22. In the present embodiment, the same component is used for each of the projection system aperture diaphragm 14 and the photodetection system aperture diaphragm 22. Description will be given below on the projection system aperture diaphragm 14.

The projection system aperture diaphragm 14 is a disk with six apertures 23a, 23b, 23c, 23d, 23e, and 23f formed on the disk. The apertures 23a, 23b, 23c, 23d, 23e, and 23f are arranged at positions by dividing the same circumference in six equal parts. The diameter of each of the apertures is set to about φ1 mm to φ8 mm by giving consideration on the size of a pupil. For example, φ1 mm, φ2 mm, φ3 mm, φ4 mm, φ5 mm, and φ6 mm are selected.

The projection system aperture diaphragm 14 and the photodetection system aperture diaphragm 22 are designed as rotatable so that the center of each of the apertures 23a, 23b, 23c, 23d, 23e and 23f is aligned with the optical axis of the projection optical system 2 or the optical axis of the photodetection optical system 3. The projection system aperture diaphragm 14 and the photodetection system aperture diaphragm 22 are intermittently rotated at every 60° by a stepping motors (not shown), for instance, so that an adequate aperture can be selected from 23a, 23b, 23c, 23d, 23e, and 23f. Specifically, the set of the projection system aperture diaphragm 14 and the stepping motor or the set of the photodetection system aperture diaphragm 22 and the stepping motor makes up an aperture selecting means respectively. Also, each stepping motor is independently controlled by the control unit 28 as described later. The projection system aperture diaphragm 14 and the photodetection system aperture diaphragm 22 may be designed as rotatable by a servo-motor, or the projection system aperture diaphragm 14 and the photodetection system aperture diaphragm 22 may be designed as slidable and may be linearly and intermittently moved by a linear motor and by a stepping cylinder.

The apertures 23a, 23b, 23c, 23d, 23e, and 23f are selected to match the diameter of the pupil of a subject under test. By changing the diameter of the aperture 23 selected at the projection system aperture diaphragm 14 with respect to the diameter of the aperture 23 selected at the photodetection system aperture diaphragm 22, for instance, by setting larger the diameter of the aperture 23 selected at the photodetection system aperture diaphragm 22 with respect to the diameter of the aperture 23 selected at the projection system aperture diaphragm 14, it is possible to calculate PTF (Phase Transfer Function) from the image obtained at the photoelectric detector 21.

The photoelectric detector 21 is, for instance, a CCD photodetection sensor, etc. having a photodetection surface which is an assembly of pixels. Based on a photodetection signal, a position of each pixel within the photodetection surface, configuration of an image on the photodetection surface, etc. can be detected. The position of each pixel and the configuration can be determined by setting coordinates on the photodetection surface and by calculating coordinate values of each pixel.

The photodetection signal from the photoelectric detector 21 can be stored in a storage unit 27 via a signal processing unit 26. The writing of the data from the signal processing unit 26 to the storage unit 27 is controlled by the control unit 28. As described above, the control unit 28 controls the driving mechanism and fulfills the function as an eye's optical characteristics calculating means. The control unit 28 comprises a simulation image calculating unit and a visual acuity calculation unit. Based on the data stored in the storage unit 27, calculation as required is performed, and the results of the calculation are displayed on a display unit 29. Also, in the storage unit 27, there are stored a sequence program for carrying out measurement, an image processing program for processing image signals from the photoelectric detector 21 and the photoelectric detector 37, a photodetection image judging program for judging conditions of photodetection image based on a signal from the photoelectric detector 21, a calculation program for calculating eye's optical characteristics based on the photodetection signal from the photoelectric detector 21, further, an ocular refractive power measuring program for calculating ocular refractive power and pupil diameter based on the photodetection signal from the photoelectric detector 37 as described later, and so on.

Now, description will be given on the ocular refractive power measuring unit 30. The ocular refractive power measuring unit 30 measures ocular refractive power of the eye under test 1 and also measures a pupil diameter of the eye under test 1 from the results of observation on an anterior ocular segment. The ocular refractive power measuring unit 30 has a composition equivalent to that of a conventional objective type ocular refractive power measuring system.

A half-mirror 34 is arranged on the optical axis 38 of the ocular refractive power measuring unit. A relay lens 33 and a light source 32 are arranged on an optical axis of a reflection light from the half-mirror 34. A relay lens 35, an image forming lens 36, and the photoelectric detector 37 are arranged on an optical axis of a transmission light from the half-mirror 34.

The light source 32 and the relay lens 33 make up together a target projection optical system 40 for measuring refractive degree, which projects the target image to obtain refractive degree to the fundus of the eye under test. A luminous flux of the target image from the light source 32 being the target is in form of a complete round ring, and the luminous flux is projected to the fundus of the eye under test 1 via the half-mirrors 34 and 31.

The relay lens 35, the image forming lens 36 and the photoelectric detector 37 make up together a photodetection optical system 41 for measuring refractive degree. The photodetection system 41 for measuring refractive degree guides a luminous flux reflected by the fundus of the eye under test 1 and passing through the half-mirrors 31 and 34 toward the photoelectric detector 37 via the relay lens 35 and the image forming lens 36.

The photoelectric detector 37 is also designed to be able to take an image of an anterior ocular segment of the eye under test 1 so that an image of the anterior ocular segment can be obtained when ocular refractive power is measured or eye's optical characteristics are measured as described later.

The photodetection signal of the image obtained at the photoelectric detector 37 is inputted to the control unit 28 via the signal processing unit 26. Based on the photodetection signal from the photoelectric detector 37, the control unit 28 calculates ocular refractive power, and a pupil diameter of the eye under test 1 is calculated by the required means such as image processing. The calculated ocular refractive power and the calculated pupil diameter of the eye under test are stored in the storage unit 27.

In the image processing for calculating the pupil diameter, for instance, photodetection intensity is different between a photodetection luminous flux from a portion of the pupil and a photodetection luminous flux from a portion of an iris around the pupil. In this respect, a position of the boundary between the pupil and the iris is obtained from light intensity distribution on a line traversing the pupil, and the pupil diameter is calculated from the position of the boundary thus obtained.

Based on the pupil diameter of the eye under test thus calculated, optimal apertures are selected from the apertures 23a, 23b, 23c, 23d, 23e, and 23f.

Description will be given below on operation of the above optical systems.

While the eye under test 1 is gazing at the fixation target 15, a target image is projected from the light source 32. The target image reflected by the fundus of the eye under test 1 is received by the photoelectric detector 37, and the control unit 28 calculates ocular refractive power based on the photodetection signal from the photoelectric detector 37. Also, an image of an anterior ocular segment is acquired by the photoelectric detector 37, and the control unit 28 calculates a pupil diameter of the eye under test 1 from the image of the anterior ocular segment.

While the eye under test 1 is gazing at the fixation target 15, a spot-like projection luminous flux is projected by the projection optical system 2. Visible light is used for the fixation target 15, and infrared light is used for the projection luminous flux.

Based on the results of measurement, the control unit 28 controls stepping motors (not shown) and rotates the projection system aperture diaphragm 14 and the photodetection system aperture diaphragm 22, and apertures optimal for the pupil diameter of the eye under test 1 are selected from the apertures 23a, 23b, 23c, 23d, 23e, and 23f. Also, based on the measured ocular refractive power, positions of the light source unit 4 and the focusing lens 19 are adjusted, and an image is formed by the reflection light from the fundus of the eye under test 1 on the photoelectric detector 21 to match the ocular refractive power of the eye under test 1.

The projected luminous flux (infrared light) emitted from the light source 5 passes through the relay lens 6 and the half-mirror 7. A transmitted projected luminous flux has its luminous flux diameter restricted by the projection system aperture diaphragm 14. The luminous flux reaches the polarization beam splitter 8 and the S-linearly polarized light component is reflected by the polarization beam splitter 8. The luminous flux passes through the relay lens 9 and is projected to the fundus of the eye under test 1 via the ¼ wave plate 13 by the objective lens 11, and a primary target image is formed as a point image.

When the S-linearly polarized light passes through the ¼ wave plate 13, the S-linearly polarized light is turned to a right circularly polarized light. The projected luminous flux is reflected by the fundus of the eye under test 1, and the reflected luminous flux is a left circularly polarized light through the reflection by the fundus. Further, when the reflected luminous flux passes through the ¼ wave plate 13, the reflected luminous flux is turned to a P-linearly polarized light, which has a direction of polarization by 90° different from that of the S-linearly polarized light.

The P-linearly polarized light is guided toward the polarization beam splitter 8 by the objective lens 11 and the relay lens 9. The polarization beam splitter 8 reflects the S-linearly polarized light and allows the P-linearly polarized light to pass. Thus, the reflected luminous flux passes through the polarization beam splitter 8, and a diameter of photodetection luminous flux is determined by the photodetection system aperture diaphragm 22. After passing through the photodetection system aperture diaphragm 22, an image of the reflected luminous flux is formed as a secondary target image by the focusing lens 19 and the image forming lens 20 on the photoelectric detector 21.

Light intensity distribution of the secondary target image received by the photoelectric detector 21 reflects optical characteristics of the eye under test 1. By detecting photodetecting condition of the photoelectric detector 21, eye's optical characteristics can be measured.

Figure 4:
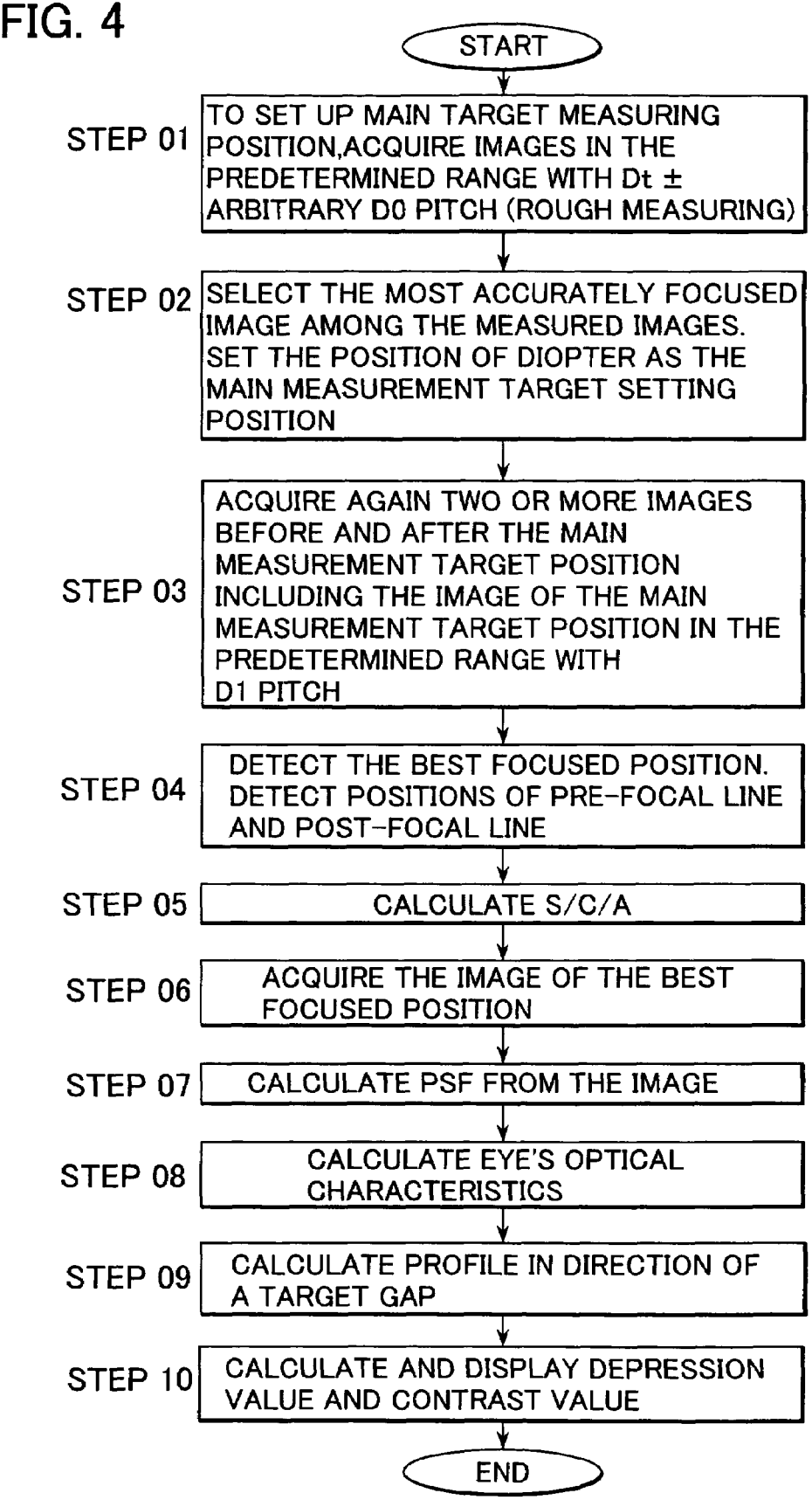
FIG. 4 is a flow chart to show processes of measurement of eye's optical characteristics in a first embodiment of the present invention.

Now, description will be given on a flow of processes of a first embodiment of the measurement of eye's optical characteristics referring to FIG. 4.

Refractive degree (spherical degree S) of the eye under test 1 of a subject under test is preparatively measured by the ocular refractive power measuring unit 30, and a pupil diameter of the eye under test 1 is calculated by image processing from an image of an anterior ocular segment.

According to the refractive degree measured preparatively, positions of the light source unit 4 and the focusing lens 19 are adjusted. The stepping motors (not shown) are controlled, and the projection system aperture diaphragm 14 and the photodetection system aperture diaphragm 22 are rotated, and the required apertures 23 are selected. By adjusting the light source unit 4 and the focusing lens 19, an approximate target value Dt of the ocular refractive power to be measured is set up.

(Step 01) When the approximate target value Dt is set up, main measurement (rough measurement) is performed based on the approximate target value Dt. With the approximate target value Dt at the center, as many photodetection images as required are taken within a required range from the photoelectric detector 21 with a required pitch of the ocular refractive power (hereinafter referred as "D0 pitch"). An example of the image thus taken is shown in FIG. 5.

Figure 3:
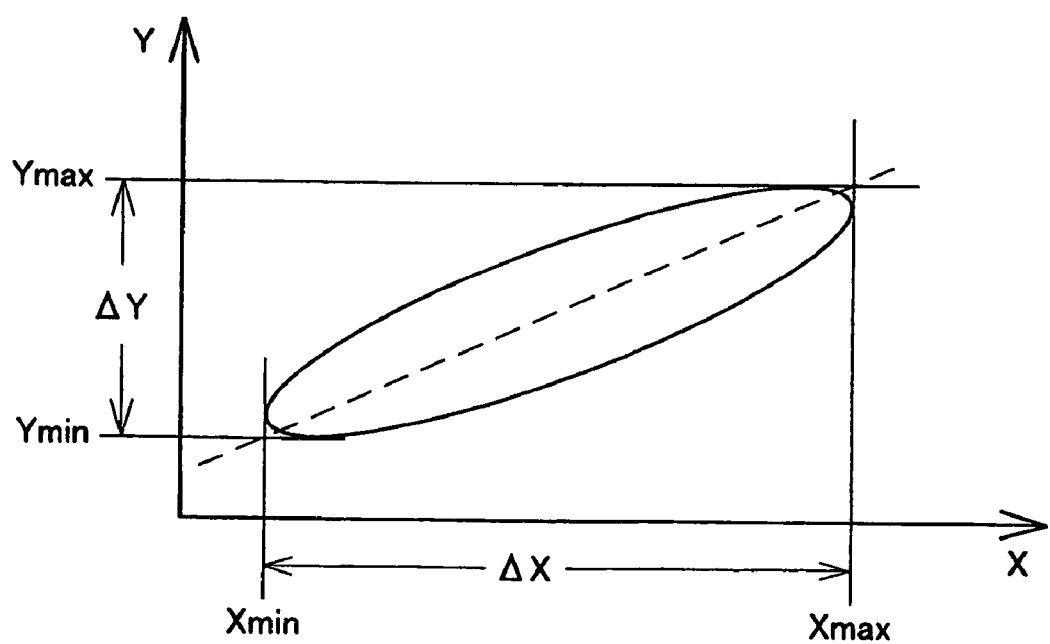
FIG. 3 is a diagram to explain a method when ocular refractive degree, astigmatic degree, and an astigmatic axis angle are measured from a taken image.
Figure 5:
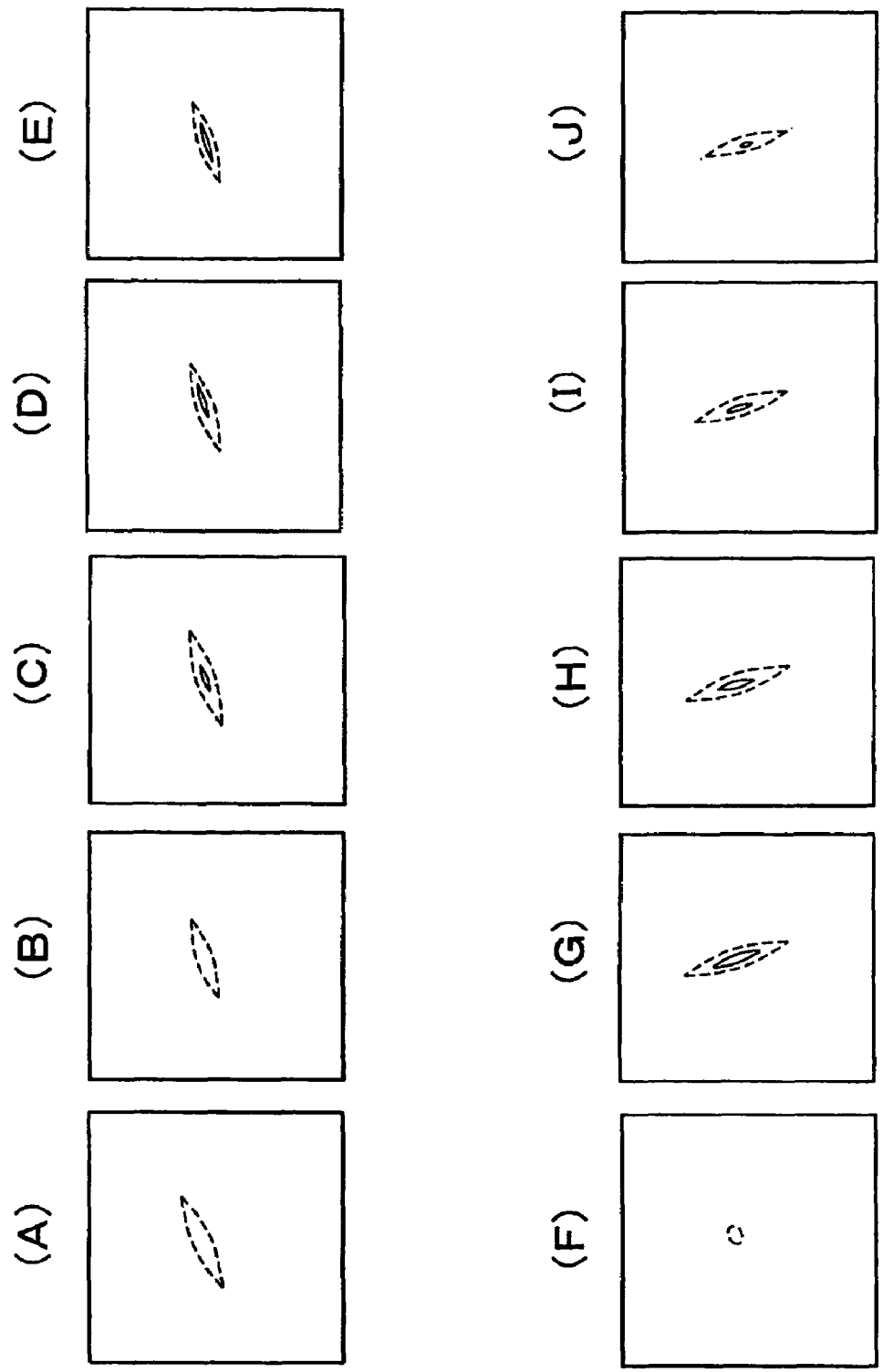
FIG. 5(A), FIG. 5(B), FIG. 5(C), FIG. 5(D), FIG. 5(E), FIG. 5(F), FIG. 5(G), FIG. 5(H), FIG. 5(I), and FIG. 5(J) each shows an image taken in the embodiment of the present invention.

(Step 02) From the images thus taken, e.g. from the images shown in FIG. 5, the most accurately focused image is selected. As the method to select the image, X-Y coordinates are set up on the image as shown in FIG. 3. From the image, the values of Xmax and Xmin as well as Ymax and Ymin are detected. Further, the values of ΔX and ΔY are obtained from the following equations:

$$(X\max - X\min) = \Delta X$$

$$(Y\max - Y\min) = \Delta Y$$

It is supposed that the most accurately focused image is obtained at a refractive degree (spherical degree S) at which the least blurred circle is formed. When the value of ΔY/ΔX (=K) is closest to 1 (hereinafter referred as "K1"), and when ΔX or ΔY is the minimum value, it is judged that focusing is most accurately performed. In FIG. 5, for instance, FIG. 5(F) shows the most accurately focused image.

(Step 03) The refractive degree, at which K1 is obtained, is set up again as a new precise target value, and main measurement (precise measurement) is performed again. As many images as required before and after the precise target position including an image of the precise target position are acquired with D1 pitch, which is smaller than D0 pitch as described above. The setting of the number of images to be acquired can be calculated based on the configuration of the image etc. obtained by rough measurement.

(Step 04) Similar to the procedure in Step 02, it is evaluated whether the taken image is accurately focused or not. Among the images acquired with D1 pitch, the image is selected, which has the smallest value of K1 and the smallest value of ΔX or of ΔY, and it is judged that the position where K1 takes the smallest value and where ΔX or ΔY takes the smallest value, is the best focused position.

Next, as the measurement of astigmatism, refractive degree of a pre-focal line and a post-focal line are measured. Regarding the pre-focal line and the post-focal line, the pre-focal line is defined, for instance, as having a refractive degree where the value of ΔX is at the minimum and the value of ΔY/ΔX is at the maximum. Also, the post-focal line is defined as having a refractive degree where the value of ΔY is at the minimum and the value of ΔY/ΔX is at the minimum.

(Step 05) By obtaining the refractive degree of the best focused position (the least blurred circle), the refractive degree of the best focused position is measured as the refractive degree (spherical degree S) of the eye under test 1. When the value of refractive degree Df to match the image at the pre-focal line and the value of refractive degree Db to match the image of post-focal line are obtained, astigmatic degree (cylindrical refractive degree C) is obtained by the equation: (Df−Db).

Further, tilting in the image of the pre-focal line and tilting in the image of the post-focal line respectively indicate tilting of an astigmatic axis. The astigmatic axis is a straight line connecting two points: (Xmax, Ymax) and (Xmin, Ymin). Also, an astigmatic axis angle Ax on the pre-focal line and an astigmatic axis angle Ay on the post-focal line can be obtained respectively by calculating the value of $\tan^{-1}(\Delta Y/\Delta X)$ from the images on the pre-focal line and the post-focal line. From the taken image, the value of S/C/A is calculated for the astigmatism of the eye under test 1.

When the value of S/C/A is measured for the astigmatism of the eye under test 1 described above, the reflected luminous flux is hardly not influenced by factors such as configuration of a cornea, an edema, turbidity of a crystalline lens, etc. because the luminous flux of the target image projected to the eye under test 1 is in spot-like shape. Thus, measurement of astigmatism can be performed regardless of the conditions of the eye under test 1, and accurate measurement of astigmatism can be performed.

Further, as shown in Step 06 to Step 10, according to the present invention, the target image projected to the fundus of the eye under test 1 can be objectively observed by image processing.

(Step 06) The image at the best focused position is selected as an image for calculating the eye's optical characteristics.

(Step 07 and Step 08) On the image thus selected, eye's optical characteristics such as PSF are calculated. From the eye's optical characteristics thus obtained, a simulation image of the target image projected to the fundus of the eye under test is calculated.

(Step 09) On the simulation image calculated in Step 08, a profile in direction of a target gap is calculated.

(Step 10) Further, a depression value and a contrast value are calculated. The simulation image, the depression value, and the contrast value thus calculated are displayed on the display unit 29.

The calculations of eye's optical characteristics such as PSF, the profile in direction of the target gap, the depression value and the contrast value in Step 07 to Step 10 are described in the Japanese Patent Publication JP-A-2002-209852 already filed.

In the first embodiment as described above, the image of the anterior ocular segment for the measurement of the pupil diameter of the eye under test is taken by the ocular refractive power measuring unit 30, while the image may be taken by the projection optical system 2 and by the photo-detection optical system 3. The light source unit 4 and the focusing lens 19 are arranged at the positions of the preset refractive degree. Under this condition, the light source 5 is turned on to illuminate the anterior ocular segment. The image of the anterior ocular segment is obtained by the photoelectric detector 21, and the pupil diameter of the eye under test 1 is calculated through image processing of the acquired image.

Next, description will be given on a flow of processes of a second embodiment of the measurement of eye's optical characteristics.

(Step 01) Rough measurement is performed by the ocular refractive power measuring unit 30. In addition to the measurement of ocular refractive degree (S), rough measurement is performed on astigmatic degree (C) and astigmatic axis (A). For the measurement of astigmatic degree (C) and astigmatic axis (A), a projected target image of a complete round ring reflected by the fundus is received by the photoelectric detector 37, and based on configuration (i.e. elliptical shape) of the received target image, astigmatic degree (C) and astigmatic axis (A) are measured.

(Step 02) Based on the ocular refractive degree (S), the astigmatic degree (C) and the astigmatic axis (A) obtained through rough measurement by the ocular refractive power measuring unit 30, a precise target value for carrying out the precise measurement is determined, and the range of the taken image refractive degree is decided for precise measurement based on the astigmatic degree (C) and the astigmatic axis (A).

(Step 03) The precise target value is set up, and precise measurement is performed. As many images as required before and after precise target position including an image of the precise target position are acquired with D1 pitch in the determined range. The setting of the number of the images to be acquired is calculated based on the configuration, etc. of the images obtained by rough measurement.

Based on the acquired images and according to the procedures of Step 04 to Step 10, the ocular refractive degree (S), the astigmatic degree (C) and the astigmatic axis (A) are calculated. Further, eye's optical characteristics such as PSF are calculated, and the depression value and the contrast value are also calculated.

The procedures of Step 04 to Step 10 are the similar to the operations explained in connection with FIG. 4, and detailed description is not given here.

In the second embodiment, the processes such as taking images in rough measurement of the first embodiment can be omitted. As a result, the time required for measurement can be reduced and the burden on the subject under test can be alleviated.

According to the present invention, regardless of the conditions of the eye under test, measurement of astigmatism can be performed, and accurate measurement can be performed without being influenced hardly by configuration of a cornea, an edema, turbidity of a crystalline lens, etc. Also, by processing the taken image, the ocular refractive degree, the astigmatic degree, and the astigmatic axis etc. are measured. Further, the image at the fundus of the eye under test can be simulated. As a result, measuring procedure by the examiner can be extensively simplified, and measurement can be performed with high efficiency. Also, measurement error due to individual difference of the examiner can be eliminated, and measurement results can be obtained with high reproducibility and high reliability.

What is claimed is:

1. An eye's optical characteristics measuring system, comprising a first target projection optical system for projecting a target image on a fundus of an eye under test, a first photodetecting means for receiving the target image reflected from the fundus of the eye under test from said first target projection optical system, an ocular refractive power measuring unit for measuring ocular refractive power of the eye under test based on the photodetection result from said first photodetecting means, a second target projection optical system for projecting a spot-like target image to the fundus of the eye under test, a second photodetecting means for receiving the target image reflected from the fundus of the eye under test, and an eye's optical characteristics measuring unit for measuring ocular refractive power based on two or more images acquired at a predetermined refractive degree pitch before and after centering the value of the refractive degree of the eye under test obtained by said second photodetecting means.

2. An eye's optical characteristics measuring system according to claim 1, wherein said eye's optical characteristics measuring unit comprises means for measuring the spherical refractive power based on an image having a least blurred circle among the two or more images.

3. An eye's optical characteristics measuring system according to claim 1, wherein said eye's optical characteristics measuring unit comprises means for measuring cylindrical refractive degree, among the two or more images, from a difference between refractive degree corresponding to the image of a pre-focal line and refractive degree corresponding to the image of a post-focal line, and means for measuring an astigmatic axis angle based on configurations of the image of a pre-focal line and the image of the post-focal line.

4. An eye's optical characteristics measuring system according to claim 1, wherein said eye's optical characteristics measuring unit comprises a calculating means for obtaining light intensity distribution based on the image acquired by said second photodetecting means and for calculating a simulation image of the target image projected on the fundus of the eye under test from the light intensity distribution thus obtained.

5. An eye's optical characteristics measuring system according to claim 4, wherein said calculating means detects light intensity distribution characteristics in a predetermined meridional direction of the simulation image.

6. An eye's optical characteristics measuring method, comprising a first step of projecting a target image on a fundus of an eye under test, a second step of receiving the target image reflected from the fundus of the eye under test from a first target projection optical system, a third step of measuring ocular refractive power of the eye under test based on photodetection result, a fourth step of projecting a spot-like target image to the fundus of the eye under test, a fifth step of receiving the target image reflected from the fundus of the eye under test, a sixth step of acquiring two or more images at a predetermined refractive degree pitch before and after centering the value of the refractive degree of the eye under test obtained, and a seventh step of measuring ocular refractive power based on two or more images acquired.

7. An eye's optical characteristics measuring method according to claim 6, further comprising an eighth step of measuring spherical refractive power based on an image having a least blurred circle among said two or more images.

8. An eye's optical characteristics measuring method according to claim 6, further comprising a ninth step of measuring cylindrical refractive degree, among the two or more images, from a difference between the refractive degree corresponding to the image of a pre-focal line and the refractive degree corresponding to the image of a post-focal line, and measuring an astigmatic axis angle based on configurations of the image of said pre-focal line and the image of said post-focal line.

* * * * *